(12) United States Patent
Schmiesing

(10) Patent No.: US 6,642,246 B1
(45) Date of Patent: Nov. 4, 2003

(54) QUINUCLIDINE ACRYLAMIDES

(75) Inventor: Richard Schmiesing, Wilmington, DE (US)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 10/110,663

(22) PCT Filed: Oct. 13, 2000

(86) PCT No.: PCT/SE00/01993
§ 371 (c)(1),
(2), (4) Date: Apr. 15, 2002

(87) PCT Pub. No.: WO01/29034
PCT Pub. Date: Apr. 26, 2001

(30) Foreign Application Priority Data

Oct. 18, 1999 (SE) ................................................ 9903760

(51) Int. Cl.[7] .................... A61K 31/439; A61K 31/46; C07D 453/02; C07D 451/04; A61P 25/00
(52) U.S. Cl. .................... 514/274; 514/305; 514/304; 514/412; 514/414; 514/299; 544/316; 546/133; 546/112; 546/121; 546/124; 546/125; 546/126; 548/452; 548/465
(58) Field of Search ................................. 546/133, 112, 546/121, 124, 125, 126; 548/452, 465; 544/316; 514/305, 304, 412, 414, 274

(56) References Cited

U.S. PATENT DOCUMENTS 5,686,461 A * 11/1997 Cugola et al. ............... 514/278

FOREIGN PATENT DOCUMENTS

| EP | 581165 A2 | 2/1994 | |
|---|---|---|---|
| WO | WO 9420465 A1 | 9/1994 | |
| WO | WO9621644 | 7/1996 | |
| WO | WO 9711072 A1 * | 3/1997 | C07D/453/02 |
| WO | WO 9801443 A1 | 1/1998 | |

OTHER PUBLICATIONS

Gopalakrishnan M et al. Eur. J. Pharm. (1995) Molecular Pharmacology Section 290, 237–246.*
STN International, File CAPLUS asccession No. 1995:904880, Document No. 124:649,Kostochka, L.M. et al: "Synthesis and local anesthetic activity of tropane enamides and amides"; & Khim.–Farm. Zh. (1995), 29 (3), 40–2.

* cited by examiner

Primary Examiner—Evelyn Mei Huang
(74) Attorney, Agent, or Firm—Kenneth F. Mitchell

(57) ABSTRACT

Compounds of formula I

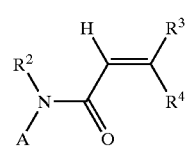

wherein A represents:

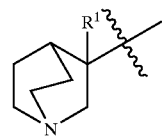

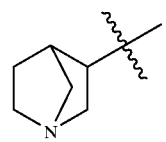

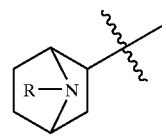

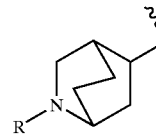

or

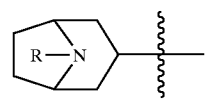

and R, $R^1$, $R^2$, $R^3$ and $R^4$ are as defined in the specification, pharmaceutically-cceptable salts thereof, processes for preparing them, pharmaceutical compositions containing them and their use in therapy, especially in the treatment or prophylaxis of psychotic disorders and intellectual impairment disorders.

12 Claims, No Drawings

QUINUCLIDINE ACRYLAMIDES

CROSS REFERENCE TO RELATED APPLICATIONS

This is a 371 filing of PCT Application PCT/SE00/01993 filed Oct. 13, 2000, pending, which claim priority under the Paris Convention of Application No. 9903760-8 filed in Sweden on Oct. 18, 1999.

TECHNICAL FIELD

This invention relates to novel quinuclidine acrylamides or pharmaceutically acceptable salts thereof, processes for preparing them, pharmaceutical compositions containing them and their use in therapy. A further object is to provide active compounds that are potent ligands for nicotinic acetylcholine receptors (nAChRs).

BACKGROUND OF THE INVENTION

The use of compounds which bind nicotinic acetylcholine receptors in the treatment of a range of disorders involving reduced cholinergic function such as Alzheimer's disease, cognitive or attention disorders, anxiety, depression, smoking cessation, neuroprotection, schizophrenia, analgesia, Tourette's syndrome, and Parkinson's disease has been discussed in McDonald et al. (1995) "Nicotinic Acetylcholine Receptors: Molecular Biology, Chemistry and Pharmacology", Chapter 5 in Annual Reports in Medicinal Chemistry, vol. 30, pp. 41–50, Academic Press Inc., San Diego, Calif.; and in Williams et al. (1994) "Neuronal Nicotinic Acetylcholine Receptors," Drug News & Perspectives, vol. 7, pp. 205–223.

Quinuclidine acrylamide derivatives as potential antitussive agents are known in the art, in EP-A2-581,165. Indole derivatives are known in the art, e.g. in WO94/20465.

DISCLOSURE OF THE INVENTION

According to the invention it has been found that compounds of formula I, wherein:

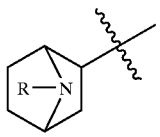

I

A represents:

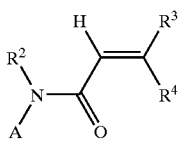

II

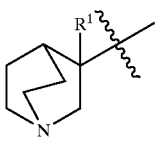

III

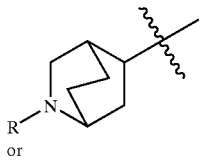

IV

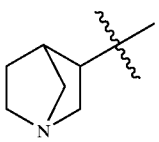

V or

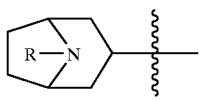

VI

R represents hydrogen or methyl;
$R^1$ and $R^2$ are independently hydrogen, or $C_1$–$C_4$ alkyl;
$R^3$ and $R^4$ are independently hydrogen, $C_1$–$C_4$ alkyl or SAr, provided that at least one of $R^3$ and $R^4$ represents SAr;
Ar represents a 5- or 6-membered aromatic or heteroaromatic ring containing zero to three nitrogen atoms, zero or one oxygen atom, and zero or one sulfur atom or an 8-, 9- or 10-membered fused aromatic or heteroaromatic ring system containing zero to four nitrogen atoms, zero to one oxygen atom, and zero to one sulfur atom which may optionally be substituted with one or more substituents selected from: hydrogen, halogen, $C_1$–$C_4$ alkyl, $C_2$–$C_4$ alkenyl, $C_2$–$C_4$ alkynyl, aryl, heteroaryl, —$CO_2R^5$, —CN, —$NO_2$, —$NR^6R^7$, —$CF_3$, —$OR^8$;
$R^5$, $R^6$, $R^7$, and $R^8$ are independently hydrogen, $C_1$–$C_4$ alkyl, aryl, heteroaryl, —C(O)$R^9$, —C(O)NH$R^{10}$, —C(O)$R^{11}$, —$SO_2R^{12}$, or,
$R^6$ and $R^7$ may together be $(CH_2)_jQ(CH_2)_k$ where Q is O, S, $NR^{13}$, or, a bond;
j is 2 to 7;
k is 0 to 2;
$R^9$, $R^{10}$, $R^{11}$, $R^{12}$, and $R^{13}$, are independently $C_1$–$C_4$ alkyl, aryl, or heteroaryl;
or an enantiomer thereof, and the pharmaceutically acceptable salts thereof are potent ligands for nicotinic acetylcholine receptors.

Unless otherwise indicated, the $C_1$–$C_4$ alkyl groups referred to herein, e.g., methyl, ethyl, n-propyl, n-butyl, i-propyl, i-butyl, t-butyl, s-butyl, whether alone or part of another group, may be straight-chained or branched, and the $C_3$–$C_4$ alkyl groups may also be cyclic, e.g., cyclopropyl, cyclobutyl.

Unless otherwise indicated, aryl refers to a phenyl ring which may optionally be substituted with one to three of the following substituents chosen from among the following: halogen, $C_{1-C4}$ alkyl, $C_2$–$C_4$ alkenyl, $C_2$–$C_4$ alkynyl, $CO_2R^7$, —CN, —$NO_2$, —$NR^8R^9$, —$CF_3$, —$OR^{10}$.

Unless otherwise indicated, heteroaryl refers to a 5- or 6-membered aromatic or heteroaromatic ring containing zero to three nitrogen atoms, zero or one oxygen atom, and zero or one sulfur atom, provided that the ring contains at least one nitrogen, oxygen, or sulfur atom, which may optionally be substituted with one or more substituents chosen from among the following: halogen, $C_1$–$C_4$ alkyl, $C_2$–$C_4$ alkenyl, $C_2$–$C_4$ alkynyl, $CO_2R^5$, —CN, —$NO_2$,— $NR^6R^7$, —$CF_3$, —$OR^8$.

Unless otherwise indicated, halogen refers to fluorine, chlorine, bromine, or iodine.

Pharmaceutically acceptable derivatives include solvates and salts. For example, the compounds of formula I can form acid addition salts with acids, such as the conventional pharmaceutically acceptable acids, for example, maleic, hydrochloric, hydrobromic, phosphoric, acetic, fumaric, salicylic, citric, lactic, mandelic, tartaric and methanesulfonic acids.

In a preferred embodiment of this aspect of the invention, is compound according to formula I, wherein A represents:

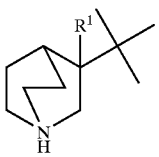

II or an enantiomer thereof, and the pharmaceutically acceptable salts thereof.

Preferred compounds of the invention include compounds of formula I wherein $R^1$, $R^2$, and one of $R^3$ or $R^4$ are hydrogen;

Preferred compounds of the invention further comprise compounds of formula I wherein Ar represents a 5- or 6-membered aromatic or heteroaromatic ring containing zero to three nitrogen atoms, zero or one oxygen atom, and zero or one sulfur atom, including phenyl, 2-pyridyl, or 2-pyrimidinyl, any of which may optionally be substituted with one or more substituents chosen from among the following: hydrogen, halogen, $C_1$–$C_4$ alkyl, $C_2$–$C_4$ alkenyl, $C_2$–$C_4$ alkynyl, —$CO_2R^5$, —CN, —$NO_2$, —$NR^6R^7$, —$CF_3$, —$OR^8$.

Preferred compounds of the invention further comprise compounds of formula I wherein Ar is an heteroaromatic ring.

Preferred compounds of the invention further comprise compounds of formula I wherein Ar is a 6-membered aromatic or heteroaromatic ring, containing zero to two nitrogen atoms.

Preferred compounds of the invention include the following:

N-(1-Aza-bicyclo[2.2.2]oct-3-yl)[Z-3-(phenylthio)propenamide]hydrochloride;
N-(1-Aza-bicyclo[2.2.2]oct-3-yl)[Z-3-(4-methylphenylthio)propenamide];
N-(1-Aza-bicyclo[2.2.2]oct-3-yl)[E-3-(4-methylphenylthio)propenamide];
N-(1-Aza-bicyclo[2.2.2]oct-3-yl)[Z-3-(3-methylphenylthio)propenamide];
N-(1-Aza-bicyclo[2.2.2]oct-3-yl)[E-3-(3-methylphenylthio)propenamide];
N-(1-Aza-bicyclo[2.2.2]oct-3-yl)[Z-3-(2-methylphenylthio)propenamide];
N-(1-Aza-bicyclo[2.2.2]oct-3-yl)[E-3-(2-methylphenylthio)propenamide];
N-(1-Aza-bicyclo[2.2.2]oct-3-yl)[Z-3-(4-methoxyphenylthio)propenamide];
N-(1-Aza-bicyclo[2.2.2]oct-3-yl)[E-3-(4-methoxyphenylthio)propenamide];
N-(1-Aza-bicyclo[2.2.2]oct-3-yl)[Z-3-(3-methoxyphenylthio)propenamide];
N-(1-Aza-bicyclo[2.2.2]oct-3-yl)[E-3-(3-methoxyphenylthio)propenamide];
N-(1-Aza-bicyclo[2.2.2]oct-3-yl)[Z-3-(2-methoxyphenylthio)propenamide];
N-(1-Aza-bicyclo[2.2.2]oct-3-yl)[E-3-(2-methoxyphenylthio)propenamide];
N-(1-Aza-bicyclo[2.2.2]oct-3-yl)[Z-3-(2-pyridylthio)propenamide];
N-(1-Aza-bicyclo[2.2.2]oct-3-yl)[E-3-(2-pyridylthio)propenamide];
N-(1-Aza-bicyclo[2.2.2]oct-3-yl)[Z-3-(4-pyridylthio)propenamide];
N-(1-Aza-bicyclo[2.2.2]oct-3-yl)[E-3-(4-pyridylthio)propenamide];
N-(1-Aza-bicyclo[2.2.2]oct-3-yl)[Z-3-(2-pyrimidinylthio)propenamide];
N-(1-Aza-bicyclo[2.2.2]oct-3-yl)[E-3-(2-pyrimidinylthio)propenamide];
N-(1-Aza-bicyclo[2.2.2]oct-3-yl)[Z-3-(2-methyl-3-furanylthio)propenamide];
N-(1-Aza-bicyclo[2.2.2]oct-3-yl)[E-3-(2-methyl-3-furanylthio)propenamide];
N-(1-Aza-bicyclo[2.2.2]oct-3-yl)[E-3-(2-imidazolylthio)propenamide];
N-(1-Aza-bicyclo[2.2.2]oct-3-yl)[Z-3-(phenylthio)-3-(methyl)propenamide];
N-(1-Aza-bicyclo[2.2.2]oct-3-yl)[Z-3-(2-benzothiazolylthio)propenamide];
N-(1-Aza-bicyclo[2.2.2]oct-3-yl)[E-3-(2-benzothiazolylthio)propenamide];
N-(1-Aza-bicyclo[2.2.2]oct-3-yl)[Z-3-(1-methyl-2-imidazolylthio)propenamide];
N-(1-Aza-bicyclo[2.2.2]oct-3-yl)[E-3-(1-methyl-2-imidazolylthio)propenamide];
N-(1-Aza-bicyclo[2.2.2]oct-3-yl)[Z-3-(5-methyl-1,3,4-thiadiazol-2-ylthio)propenamide];
N-(1-Aza-bicyclo[2.2.2]oct-3-yl)[E-3-(5-methyl-1,3,4-thiadiazol-2-ylthio)propenamide];
N-(1-Aza-bicyclo[2.2.2]oct-3-yl)[Z-3-(4-chlorophenylthio)propenamide];
N-(1-Aza-bicyclo[2.2.2]oct-3-yl)[Z-3-(2-thiazolylthio)propenamide];
N-(1-Aza-bicyclo[2.2.2]oct-3-yl)[Z-3-(2-thienylthio)propenamide];
N-(1-Aza-bicyclo[2.2.2]oct-3-yl)[E-3-(2-thienylthio)propenamide];
N-(1-Aza-bicyclo[2.2.2]oct-3-yl)[Z-3-(2-benzoxazolylthio)propenamide];
N-(1-Aza-bicyclo[2.2.2]oct-3-yl)[E-3-(2-benzoxazolylthio)propenamide];
N-(1-Aza-bicyclo[2.2.2]oct-3-yl)[Z-3-(4-trifluoromethyl-2-pyrimidinylthio)propenamide];
N-(1-Aza-bicyclo[2.2.2]oct-3-yl)[Z-3-(4-fluorophenylthio)propenamide];
N-(1-Aza-bicyclo[2.2.2]oct-3-yl)[E-3-(4-fluorophenylthio)propenamide];
N-(1-Aza-bicyclo[2.2.2]oct-3-yl)[Z-3-(2-thiazolo[4,5-b]pyridylthio)propenamide];
(R)-N-(1-Aza-bicyclo[2.2.2]oct-3-yl)[E-3-(2-thiazolo[4,5-b]pyridylthio)propenamide];
N-(1-Aza-bicyclo[2.2.2]oct-3-yl)[Z-3-(3-fluorophenylthio)propenamide];
N-(1-Aza-bicyclo[2.2.2]oct-3-yl)[E-3-(3-fluorophenylthio)propenamide];

or an enantiomer thereof, and the pharmaceutically acceptable salts thereof

Particularly preferred compounds of the invention include the following:

(R)-N-(1-Aza-bicyclo[2.2.2]oct-3-yl)[Z-3-(phenylthio)propenamide]hydrochloride;
(R)-N-(1-Aza-bicyclo[2.2.2]oct-3-yl)[Z-3-(4-methylphenylthio)propenamide];
(R)-N-(1-Aza-bicyclo[2.2.2]oct-3-yl)[E-3-(4-methylphenylthio)propenamide];
(R)-N-(1-Aza-bicyclo[2.2.2]oct-3-yl)[Z-3-(3-methylphenylthio)propenamide];
(R)-N-(1-Aza-bicyclo[2.2.2]oct-3-yl)[E-3-(3-methylphenylthio)propenamide];
(R)-N-(1-Aza-bicyclo[2.2.2]oct-3-yl)[Z-3-(9-methylphenylthio)propenamide];
(R)-N-(1-Aza-bicyclo[2.2.2]oct-3-yl)[E-3-(2-methylphenylthio)propenamide];
(R)-N-(1-Aza-bicyclo[2.2.2]oct-3-yl)[Z-3-(4-methoxyphenylthio)propenamide];
(R)-N-(1-Aza-bicyclo[2.2.2]oct-3-yl)[E-3-(4-methoxyphenylthio)propenamide];
(R)-N-(1-Aza-bicyclo[2.2.2]oct-3-yl)[Z-3-(3-methoxyphenylthio)propenamide];
(R)-N-(1-Aza-bicyclo[2.2.2]oct-3-yl)[E-3-(3-methoxyphenylthio)propenamide];
(R)-N-(1-Aza-bicyclo[2.2.2]oct-3-yl)[Z-3-(2-methoxyphenylthio)propenamide];
(R)-N-(1-Aza-bicyclo[2.2.2]oct-3-yl)[E-3-(2-methoxyphenylthio)propenamide];
(R)-N-(1-Aza-bicyclo[2.2.2]oct-3-yl)[Z-3-(2-pyridylthio)propenamide];
(R)-N-(1-Aza-bicyclo[2.2.2]oct-3-yl)[E-3-(2-pyridylthio)propenamide];
(R)-N-(1-Aza-bicyclo[2.2.2]oct-3-yl)[Z-3-(4-pyridylthio)propenamide];
(R)-N-(1-Aza-bicyclo[2.2.2]oct-3-yl)[E-3-(4-pyridylthio)propenamide];
(R)-N-(1-Aza-bicyclo[2.2.2]oct-3-yl)[Z-3-(2-pyrimidinylthio)propenamide];
(R)-N-(1-Aza-bicyclo[2.2.2]oct-3-yl)[E-3-(2-pyrimidinylthio)propenamide];
(R)-N-(1-Aza-bicyclo[2.2.2]oct-3-yl)[Z-3-(2-methyl-3-furanylthio)propenamide];
(R)-N-(1-Aza-bicyclo[2.2.2]oct-3-yl)[E-3-(2-methyl-3-furanylthio)propenamide];
(R)-N-(1-Aza-bicyclo[2.2.2]oct-3-yl)[E-3-(2-imidazolylthio)propenamide];
(R)-N-(1-Aza-bicyclo[2.2.2]oct-3-yl)[Z-3-(phenylthio)-3-(methyl)propenamide];
(R)-N-(1-Aza-bicyclo[2.2.2]oct-3-yl)[Z-3-(2-benzothiazolylthio)propenamide];
(R)-N-(1-Aza-bicyclo[2.2.2]oct-3-yl)[E-3-(2-benzothiazolylthio)propenamide];
(R)-N-(1-Aza-bicyclo[2.2.2]oct-3-yl)[Z-3-(1-methyl-2-imidazolylthio)propenamide];
(R)-N-(1-Aza-bicyclo[2.2.2]oct-3-yl)[E-3-(1-methyl-2-imidazolylthio)propenamide];
(R)-N-(1-Aza-bicyclo[2.2.2]oct-3-yl)[Z-3-(5-methyl-1,3,4-thiadiazol-2-ylthio)propenamide];
(R)-N-(1-Aza-bicyclo[2.2.2]oct-3-yl)[E-3-(5-methyl-1,3,4-thiadiazol-2-ylthio)propenamide);
(R)-N-(1-Aza-bicyclo[2.2.2]oct-3-yl)[Z-3-(4-chlorophenylthio)propenamide];
(R)-N-(1-Aza-bicyclo[2.2.2]oct-3-yl)[Z-3-(2-thiazolylthio)propenamide];
(R)-N-(1-Aza-bicyclo[2.2.2]oct-3-yl)[Z-3-(2-thienylthio)propenamide];
(R)-N-(1-Aza-bicyclo[2.2.2]oct-3-yl)[E-3-(2-thienylthio)propenamide];
(R)-N-(1-Aza-bicyclo[2.2.2]oct-3-yl)[Z-3-(2-benzoxazolylthio)propenamide];
(R)-N-(1-Aza-bicyclo[2.2.2]oct-3-yl)[E-3-(2-benzoxazolylthio)propenamide];
(R)-N-(1-Aza-bicyclo[2.2.2]oct-3-yl)[Z-3-(4-trifluoromethyl-2-pyrimidinylthio)propenamide];
(R)-N-(1-Aza-bicyclo[2.2.2]oct-3-yl)[Z-3-(4-fluorophenylthio)propenamide];
(R)-N-(1-Aza-bicyclo[2.2.2]oct-3-yl)[E-3-(4-fluorophenylthio)propenamide];
(R)-N-(1-Aza-bicyclo[2.2.2]oct-3-yl)[Z-3-(2-thiazolo[4,5-b]pyridylthio)propenamide];
(R)-N-(1-Aza-bicyclo[2.2.2]oct-3-yl)[E-3-(2-thiazolo[4,5-b]pyridylthio)propenamide];
(R)-N-(1-Aza-bicyclo[2.2.2]oct-3-yl)[Z-3-(3-fluorophenylthio)propenamide];
(R)-N-(1-Aza-bicyclo[2.2.2]oct-3-yl)[E-3-(3-fluorophenylthio)propenamide];

or an enantiomer thereof, and the pharmaceutically acceptable salts thereof.

Further particularly preferred compounds of the invention includes:

(R)-N-(1-Aza-bicyclo[2.2.2]oct-3-yl)[Z-3-(2-pyridylthio)propenamide];
(R)-N-(1-Aza-bicyclo[2.2.2]oct-3-yl)[E-3-(2-pyridylthio)propenamide];
(R)-N-(1-Aza-bicyclo[2.2.2]oct-3-yl)[Z-3-(2-pyrimidinylthio)propenamide];

or an enantiomer thereof, and the pharmaceutically acceptable salts thereof.

Methods of Preparation

In the reaction schemes and text that follow, $R^1$, $R^2$, $R^3$ and $R^4$, unless otherwise indicated, are as defined above for formula VII. The compounds of formula VII may be prepared according to the methods outlined in Scheme 1.

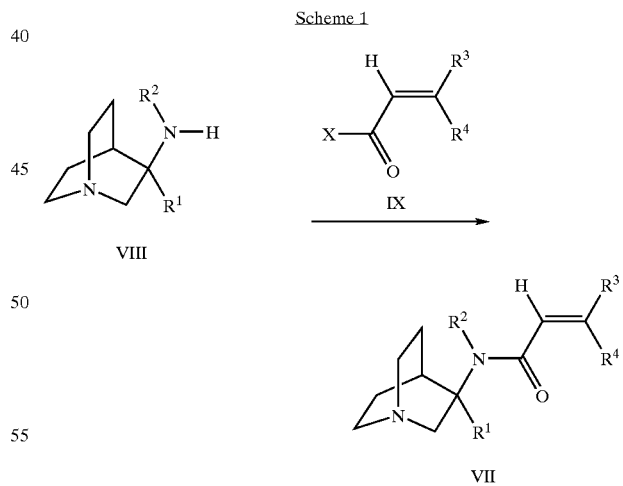

Compounds of formula I may be prepared from compounds of formula II by reaction with a compound of formula III, wherein X represents a suitable leaving group, using a suitable acylation procedure.

Suitable leaving groups X include: OH, halogen, OAlkyl, OAryl, OCOAlkyl, OCOAryl, azide. A suitable acylation procedure involves treatment of a compound of formula II with a compound of formula III at 0–120° C. in a suitable solvent. The presence of a base, or, when X=OH, a coupling agent, may also be necessary for the reaction to occur. Suitable bases for the reaction include: 4-(N,N-dimethylamino)pyridine, pyridine, triethylamine, N,N-diisopropylethylamine. The preferred base is N,N-diisopropylethylamine. Suitable coupling agents when X=OH include: carbodiimides, for example 1,3-dicyclohexylcarbodiimide or 1-(3-dimethylaminopropyl-3-ethylcarbodiimide hydrochloride; phosphonium reagents, for example benzotriazol-1-yloxytris(dimethylamino) phosphonium hexafluorophosphate or benzotriazol-1-yloxytripyrrolidinophosphonium hexafluorophosphate; and uronium reagents, for example O-benzotriazol-1-yl-N,N,N',N'-tetramethyluronium tetrafluoroborate. The preferred coupling agent is O-benzotriazol-1-yl-N,N,N',N'-tetramethyluronium tetrafluoroborate. Suitable solvents for the reaction include N,N-dimethylformamide, dimethylsulfoxide, tetrahydro-furan, or chloroform. The preferred solvent is N,N-dimethylformamide. The reaction is preferably performed at a temperature of 0–50° C., and most preferably at a temperature of 20–30° C.

Compounds of formula II in which $R^2$ represents an alkyl group may be prepared from compounds of formula II in which $R^2$ represents hydrogen by a suitable alkylation procedure.

Typical alkylation procedures include treatment with an appropriate alkyl halide or sulfonate ester and base, for example sodium hydride, in a suitable solvent, for example DMF, or reductive alkylation using the appropriate aldehyde or ketone together with a suitable reducing agent in an inert solvent. The preferred method is reductive alkylation. Suitable reducing agents include sodium borohydride and sodium cyanoborohydride. The preferred reducing agent is sodium borohydride. Suitable inert solvents include water, methanol or ethanol. The preferred solvent is methanol. The reaction is usually conducted at a temperature of 0° C. to 100° C., preferably from 20° C. to 65° C.

Compounds of formula II and III are either commercially available, or may be prepared by methods known to one skilled in the art. For example compound III may be prepared as shown in Scheme 2 according to the method described by G. Joshi, etal., Chemistry and Industry, (1991), 281.

Scheme 2

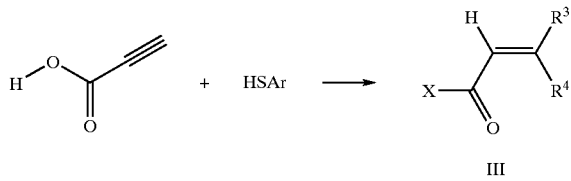

Use of compounds II and III as intermediates in a synthesis of a ligand for nicotinic acetylcholine receptors is another aspect of the invention.

Where necessary, hydroxy, amino, or other reactive groups may be protected using a protecting group as described in the standard text "Protecting groups in Organic Synthesis", $3^{rd}$ Edition (1999) by Greene and Wuts.

The above described reactions, unless otherwise noted, are usually conducted at a pressure of about one to about three atmospheres, preferably at ambient pressure (about one atmosphere). Unless otherwise stated, the above-described reactions are conducted under an inert atmosphere, preferably under a nitrogen atmosphere.

The compounds of the invention and intermediates may be isolated from their reaction mixtures by standard techniques.

Acid addition salts of the compounds of formula I which may be mentioned include salts of mineral acids, for example the hydrochloride and hydrobromide salts; and salts formed with organic acids such as formate, acetate, maleate, benzoate, tartrate, and fumarate salts.

Acid addition salts of compounds of formula I may be formed by reacting the free base or a salt, enantiomer or protected derivative thereof, with one or more equivalents of the appropriate acid. The reaction may be carried out in a solvent or medium in which the salt is insoluble or in a solvent in which the salt is soluble, e.g., water, dioxane, ethanol, tetrahydrofuran or diethyl ether, or a mixture of solvents, which may be removed in vacuum or by freeze drying. The reaction may be a metathetical process or it may be carried out on an ion exchange resin.

The compounds of formula I exist in tautomeric or enantiomeric forms, all of which are included within the scope of the invention. The various optical isomers may be isolated by separation of a racemic mixture of the compounds using conventional techniques, e.g. fractional crystallization, or chiral HPLC. Alternatively the individual enantiomers may be made by reaction of the appropriate optically active starting materials under reaction conditions which will not cause racemization.

Pharmaceutical Compositions

A further aspect of the invention relates to a pharmaceutical composition for treating or preventing a condition or disorder as exemplified below arising from dysfunction of nicotinic acetylcholine receptor neurotransmission in a mammal, preferably a human, comprising an amount of a compound of formula I, an enantiomer thereof and/or a pharmaceutically acceptable salt thereof, effective in treating or preventing such disorder or condition and an inert pharmaceutically acceptable carrier.

For the above-mentioned uses the dosage administered will, of course, vary with the compound employed, the mode of administration and the treatment desired. However, in general, satisfactory results will be obtained when the compounds of the invention are administered at a daily dosage of from about 0.1 mg to about 20 mg per kg of mammalian body weight, preferably given in divided doses 1 to 4 times a day or in sustained release form. For man, the total daily dose is in the range of from 5 mg to 1,400 mg, more preferably from 10 mg to 100 mg, and unit dosage forms suitable for oral administration comprise from 2 mg to 1,400 mg of the compound admixed with a solid or liquid pharmaceutical carrier or diluent.

The compounds of formula I or an enantiomer thereof and/or pharmaceutically acceptable salts thereof, may be used on their own or in the form of appropriate medicinal preparations for enteral, parenteral, oral, rectal or nasal administration. According to a further aspect of the invention, there is provided a pharmaceutical composition preferably comprising less than 80% and more preferably less than 50% by weight of a compound of the invention in admixture with an inert pharmaceutically acceptable diluent or carrier.

Examples of suitable diluents and carriers are:
  for tablets and dragees: lactose, starch, talc, stearic acid;
    for capsules: tartaric acid or lactose;
    for injectable solutions: water, alcohols, glycerin, vegetable oils; for suppositories: natural or hardened oils or waxes.

There is also provided a process for the preparation of such a pharmaceutical composition which comprises mixing the ingredients simultaneously or sequentially.

Utility

A further aspect of the invention is the use of a compound according to the invention, an enantiomer thereof or a pharmaceutically acceptable salt thereof, in the manufacture of a medicament for the treatment or prophylaxis of one of the below mentioned diseases or conditions; and a method of treatment or prophylaxis of one of the below mentioned diseases or conditions, which comprises administering a therapeutically effective amount of a compound according to the invention, or an enantiomer thereof or a pharmaceutically acceptable salt thereof, to a patient.

Compounds according to the invention are agonists of nicotinic acetylcholine receptors. While not being limited by theory, it is believed that agonists of the α7 nAChR (nicotinic acetylcholine receptor) subtype should be useful in the treatment or prophylaxis of psychotic disorders and intellectual impairment disorders, and have advantages over compounds which are or are also agonists of the α4 nAChR subtype. Therefore, compounds which are selective for the α7 nAChR subtype are preferred. The compounds of the invention are selective for the α7 nAChR subtype. The compounds of the invention are intended as pharmaceuticals, in particular in the treatment or prophylaxis of psychotic disorders and intellectual impairment disorders. Examples of psychotic disorders include schizophrenia, mania and manic depression, and anxiety. Examples of intellectual impairment disorders include Alzheimer's disease, learning deficit, cognition deficit, attention deficit, memory loss, Lewy Body Dementia, and Attention Deficit Hyperactivity Disorder. The compounds of the invention may also be useful as analgesics in the treatment of pain (including chronic pain) and in the treatment or prophylaxis of Parkinson's disease, Huntington's disease, Tourette's syndrome, and neurodegenerative disorders in which there is loss of cholinergic synapses. The compounds may further be indicated for the treatment or prophylaxis of jetlag, for use in inducing the cessation of smoking, and for the treatment or prophylaxis of nicotine addiction (including that resulting from exposure to products containing nicotine).

It is also believed that compounds according to the invention are useful in the treatment and prophylaxis of ulcerative colitis.

Pharmacology

The pharmacological activity of the compounds of the invention may be measured in the tests set out below:

Test A—Assay for Affinity at α7 nAChR Subtype $^{125}$I-α-Bungarotoxin (BTX) binding to rat hippocampal membranes. Rat hippocampi were homogenized in 20 volumes of cold homogenization buffer (HB: concentrations of constituents (mM): tris(hydroxymethyl)aminomethane 50; $MgCl_2$ 1; NaCl 120; KCl 5: pH 7.4). The homogenate was centrifuged for 5 minutes at 1000 g, the supernatant was saved and the pellet re-extracted. The pooled supernatants were centrifuged for 20 minutes at 12,000 ×g, washed, and resuspended in HB. Membranes (30–80 µg) were incubated with 5 nM [$^{125}$I]α-BTX, 1 mg/mL BSA (bovine serum albumin), test drug, and either 2 mM $CaCl_2$ or 0.5 mM EGTA [ethylene glycol-bis(β-aminoethylether)] for 2 hours at 21° C., and then filtered and washed 4 times over Whatman glass fibre filters (thickness C) using a Brandel cell harvester. Pretreating the filters for 3 hours with 1% (BSA/0.01% PEI (polyethyleneimine)) in water was critical for low filter blanks (0.07% of total counts per minute). Nonspecific binding was described by 100 µM (–)-nicotine, and specific binding was typically 75%.

Test B—Assay for Affinity to the α4 nAChR Subtype

[$^3$H]-(–)-nicotine binding. Using a procedure modified from Martino-Barrows and Kellar(Mol Pharm (1987) 31:169–174), rat brain (cortex and hippocampus) was homogenized as in the [$^{125}$I]α-BTX binding assay, centrifuged for 20 minutes at 12,000 ×g. washed twice, and then resuspended in HB containing 100 µM diisopropyl fluorophosphate. After 20 minutes at 4° C., membranes (approximately 0.5 mg) were incubated with 3 nM [3H]-(–)-nicotine, test drug, 1 µM atropine, and either 2 mM $CaCl_2$ or 0.5 mM EGTA for 1 hour at 4° C., and then filtered over Whatman glass fibre filters (thickness C) (pretreated for 1 hour with 0.5% PEI) using a Brandel cell harvester. Nonspecific binding was described by 100 µM carbachol, and specific binding was typically 84%.

Binding Data Analysis for Tests A and B $IC_{50}$ values and pseudo Hill coefficients ($n_H$) were calculated using the non-linear curve fitting program ALLFIT (DeLean A, Munson P J and Rodbard D (1977) Am. J. Physiol., 235:E97–E102). Saturation curves were fitted to a one site model, using the non-linear regression program ENZFITTER (Leatherbarrow, R. J. (1987)), yielding $K_D$ values of 1.67 and 1.70 nM for the $^{125}$I-α-BTX and [$^3$H]-(–)-nicotine ligands respectively. $K_i$ values were estimated using the general Cheng-Prusoff equation:

$$Ki=[IC_{50}]/((2+([\text{ligand}]/K_D])^n)^{1/n}-1)$$

where a value of n=1 was used whenever $n_H$<1.5 and a value of n=2 was used when $n_H \geq 1.5$. Samples were assayed in triplicate and were typically ±5%. $K_i$ values were determined using 6 or more drug concentrations. The compounds of the invention are compounds with binding affinities ($K_i$) of less than 1000 nNM in either Test A or Test B, indicating that they are expected to have useful therapeutic activity.

General Experimental Procedures

Commercial reagents were used without further purification. Mass spectra were recorded using either a Hewlett Packard 5988A or a MicroMass Quattro-1 Mass Spectrometer and are reported as m/z for the parent molecular ion. Room temperature refers to 20–25° C.

EXAMPLES

The following examples are preferred non-limiting examples embodying preferred aspects of the invention.

Example 1

(R)-N-(1-Aza-bicyclo[2.2.2]oct-3-yl)[Z-3-(phenylthio)propenamide]hydrochloride

To a stirred solution of (R)-1-Aza-bicyclo[2.2.2]oct-3-ylamine dihydrochloride (25 g, 0.125 mol), 3-(phenylthio) acrylic acid (23.5 g, 0.13 mol), and diisopropylethylamine (90 ml) in dry DMF (600 ml) at ambient temperature was added in succession 1-hydroxybenzotriazole hydrate (17 g, 0.126 mol) and O-benzotriazol-1-yl-N.N,N',N'-tetramethyluronium tetrafluoroborate (40 g, 0.124 mol). The resulting amber-colored solution was stirred overnight, diluted with water (1 vol), and extracted with ether (2×700 ml). The aqueous phase was made basic (pH 10) with 50% aqueous sodium hydroxide and extracted with chloroform (3×700 ml). The chloroform extracts were combined, washed with water, brine, dried over sodium sulfate and concentrated to dryness to give crude product as a syrup (40 g). The syrup was taken in isopropanol (IL), made acidic with gaseous HCL, and allowed to stand. The resulting solid was collected by filtration, recrystallized from isopropanol (2×), and dried in vacuo to give the title compound (8 g) as a white solid. MS (ES$^+$) 289. (MH$^{30}$).

Purification of the mother liquors from above by chromatography on silica gel using ammoniated methanol/ chloroform mixtures as the eluent gave (R)-N-(1-Aza-bicyclo[2.2.2]oct-3-yl)[E-3-(phenylthio)propenamide; MS (ES$^+$) 289. (MH$^+$).

Example 2

(R)-N-(1-Aza-bicyclo[2.2.2]oct-3yl)[Z-3-(4-methylphenylthio)propenamide] and (R)-N-(1-Aza-bicyclo[2.2.2]oct-3-yl)[E-3-(4-methylphenylthio)propenamide]

Employing essentially the same procedure as that described in Example 1 above but substituting 3-(4-methylphenylthio)acrylic acid for the 3-(phenylthio)acrylic acid and purifying by chromatography on silica gel using ammnoniated methanol/chloroform mixtures as the eluent resulted in formation of the title compounds; MS (ES$^-$) 303. (MH$^-$).

Example 3

(R)-N-(1-Aza-bicyclo[2.2.2]oct-3-yl)[Z-3-(3-methylphenylthio)propenamide] and (R)-N-(1-Aza-bicyclo[2.2.2]oct-3-yl)[E-3-(3-methylphenylthio)propenamide]

Employing essentially the same procedure as that described in Example 1 above but substituting 3-(3methylphenylthio)acrylic acid for the 3-(phenylthio)acrylic acid and purifying by chromatography on silica gel using ammoniated methanol/chloroform mixtures as the eluent resulted in formation of the title compounds; MS (ES$^-$) 303. (MH$^-$).

Example 4

R)-N-(1-Aza-bicyclo[2.2.2]oct-3-yl)[Z-3-(2-methylphenylthio)propenamide] and (R)-N-(1-Aza-bicyclo[2.2.2]oct-3-yl[E-3-(2-methylphenylthio)propenamide]

Employing essentially the same procedure as that described in Example 1 above but substituting 3-(2-methylphenylthio)acrylic acid for the 3-(phenylthio)acrylic acid and purifying by chromatography on silica gel using ammoniated methanol/chloroform mixtures as the eluent resulted in formation of the title compounds; MS (ES$^-$) 303. (MH$^-$).

Example 5

(R)-N-(1-Aza-bicyclo[2.2.2]oct-3-yl)[Z-3-(4-methoxyphenylthio)propenamide] and (R)-N-(1-Aza-bicyclo[2.2.2]oct-3-yl)[E-3-(4-methoxyphenylthio)propenamide]

Employing essentially the same procedure as that described in Example 1 above but substituting 3-(4-methoxyphenylthio)acrylic acid for the 3-(phenylthio)acrylic acid and purifying by chromatography on silica gel using ammoniated methanol/chloroform mixtures as the eluent resulted in formation of the title compounds; MS (ES$^+$) 319. (MH$^+$).

Example 6

(R)-N-(1-Aza-bicyclo[2.2.2]oct-3-yl)[Z-3-(3-methoxyphenylthio)propenamide] and (R)-N-(1-Aza-bicyclo[2.2.2]oct-3-yl)[E-3-(3-methoxyphenylthio)propenamide]

Employing essentially the same procedure as that described in Example 1 above but substituting 3-(3-methoxyphenylthio)acrylic acid for the 3-(phenylthio)acrylic acid and purifying by chromatography on silica gel using ammnoniated methanol/chloroform mixtures as the eluent resulted in formation of the title compounds; MS (ES$^+$) 319. (MH$^+$).

Example 7

(R)-N-(1-Aza-bicyclo[2.2.2]oct-3-yl)[Z-3-(2-methoxyphenylthio)propenamide] and (R)-N-(1-Aza-bicyclo[2.2.2]oct-3-yl)[E-3-(2-methoxyphenylthio)propenamide]

Employing essentially the same procedure as that described in Example 1 above but substituting 3-(2-methoxyphenylthio)acrylic acid for the 3-(phenylthio)acrylic acid and purifying by chromatography on silica gel using ammoniated methanol/chloroform mixtures as the eluent resulted in formation of the title compounds; MS (ES$^+$) 319. (MH$^+$).

Example 8

(R)-N-(1-Aza-bicyclo[2.2.2]oct-3-yl)[Z-3-(2-pyridylthio)propenamide] and (R)-N-(1-Aza-bicyclo[2.2.2]oct-3-yl)[E-3-(2-pyridylthio)propenamide]

Employing essentially the same procedure as that described in Example 1 above but substituting 3-(2-pyridylthio)acrylic acid for the 3-(phenylthio)acrylic acid and purifying by chromatography on silica gel using ammoniated methanol/chloroform mixtures as the eluent resulted in formation of the title compounds; MS (ES$^+$) 290. (MH$^+$).

Example 9

(R)-N-(1-Aza-bicyclo[2.2.2]oct-3-yl)[Z-3-(4-pyridylthio)propenamide] and (R)-N-(1-Aza-bicyclo[2.2.2]oct-3-yl)[E-3-(4-pyridylthio)propenamide]

Employing essentially the same procedure as that described in Example 1 above but substituting 3-(4-pyridylthio)acrylic acid for the 3-(phenylthio)acrylic acid and purifying by chromatography on silica gel using ammoniated methanol/chloroform mixtures as the eluent resulted in formation of the title compounds; MS (ES$^-$) 290. (MH$^-$).

Example 10

(R)-N-(1-Aza-bicyclo[2.2.2]oct-3-yl)[Z-3-(2-pyrimidinylthio)propenamide] and (R)-Ar-(1-Aza-bicyclo2.2.2]oct-3-yl)[E-3-(2-pyrimidinylthio)propenamide]

Employing essentially the same procedure as that described in Example 1 above but substituting 3-(2-pyrimidinylthio)acrylic acid for the 3-(phenylthio)acrylic acid and purifying by chromatography on silica gel using ammoniated methanol/chloroform mixtures as the eluent resulted in formation of the title compounds; MS (ES$^-$) 291. (MH$^-$).

Example 11

(R)-N-(1-Aza-bicyclo[2.2.2]oct-3-yl)[Z-3-2-methyl-3-furanylthio)propenamide] and (R)-N-(1-Aza-bicyclo[2.2.2]oct-3-yl)[E-3-(2-methyl-3-furanylthio)propenamide]

Employing essentially the same procedure as that described in Example 1 above but substituting 3-(2-methyl- 3-furanylthio)acrylic acid for the 3-(phenylthio)acrylic acid and purifying by chromatography on silica gel using ammoniated methanol chloroform mixtures as the eluent resulted in formation of the title compounds; MS (ES+) 293. (MH+).

Example 12

(R)-N-(1-Aza-bicyclo[2.2.2]oct-3-yl)[E-3-(2-imidazolylthio)propenamide]

Employing essentially the same procedure as that described in Example 1 above but substituting 3-(2-imidazolylthio)acrylic acid for the 3-(phenylthio)acrylic acid and purifying by chromatography on silica gel using ammoniated methanol/chloroform mixtures as the eluent resulted in formation of the title compound; MS (ES−) 279. (MH−).

Example 13

(R)-N-(1-Aza-bicyclo[2.2.2]oct-3-yl)[Z-3-(phenylthio)-3-(methyl)propenamide]

Employing-essentially the same procedure as that described in Example 1 above but substituting 3-(phenylthio)-3-methylacrylic acid for the 3-(phenylthio) acrylic acid and purifying by chromatography on silica gel using ammoniated methanol/chloroform mixtures as the eluent resulted in formation of the title compound; MS (ES+) 303. (MH+).

Example 14

(R)-N-(1-Aza-bicyclo[2.2.2]oct-3-yl)[Z-3-(2-benzothiazolylthio)propenamide] and (R)-N-(1-Aza-bicyclo[2.2.2]oct-3-yl)[E-3-(2-benzothiazolylthio)propenamide]

Employing essentially the same procedure as that described in Example 1 above but substituting 3-(2-benzothiazolylthio)acrylic acid for the 3-(phenylthio)acrylic acid and purifying by chromatography on silica gel using ammoniated methanol/chloroform mixtures as the eluent resulted in formation of the title compounds; MS (ES+) 346. (MH+).

Example 15

(R)-N-(1-Aza-bicyclo[2.2.2]oct-3-yl)[Z-3-(1-methyl-2-imidazolylthio)propenamide] and (R) -N-(1-Aza-bicyclo[2.2.2]oct-3-yl)[E-3-(1-methyl-2-imidazolylthio)propenamide]

Employing essentially the same procedure as that described in Example 1 above but substituting 3-(1-methyl-2-imidazolylthio)acrylic acid for the 3-(phenylthio)acrylic acid and purifying by chromatography on silica gel using ammoniated methanol/chloroform mixtures as the eluent resulted in formation of the title compounds; MS (ES+) 293. (MH+).

Example 16

(R)-N-(1-Aza-bicyclo[2.2.2]oct-3-yl)[Z-3-(5-methyl-1,3,4-thiadiazol-2-ylthio)propenamide] and (R)-N-(1-Aza-bicyclo[2.2.2]oct-3-yl)[E-3-(5-methyl-1,3,4-thiadiazol -2-ylthio)propenamide]

Employing essentially the same procedure as that described in Example 1 above but substituting 3-(5-methyl-1,3,4-thiadiazol-2-ylthio)acrylic acid for the 3-(phenylthio) acrylic acid and purifying by chromatography on silica gel using ammoniated methanol/chloroform mixtures as the eluent resulted in formation of the title compounds; MS (ES−) 311. (MH−).

Example 17

(R)-N-(1-Aza-bicyclo[2.2.2]oct-3-yl)[Z-3-(4-chlorophenylthio)propenamide]

Employing essentially the same procedure as that described in Example 1 above but substituting 3-(4-chlorophenylthio)acrylic acid for the 3-(phenylthio)acrylic acid and purifying by chromatography on silica gel using ammoniated methanol/chloroform mixtures as the eluent resulted in formation of the title compound; MS (ES+) 324,326. (MH+).

Example 18

(R)-N-(1-Aza-bicyclo[2.2.2]oct-3-yl)[Z-3-(2-thiazolylthio)propenamide]

Employing essentially the same procedure as that described in Example 1 above but substituting 3-(2-thiazolylthio)acrylic acid for the 3-(phenylthio)acrylic acid and purifying by chromatography on silica gel using ammoniated methanol/chloroform mixtures as the eluent resulted in formation of the title compound; MS (ES+) 296. (MH+).

Example 19

(R)-N-(1-Aza-bicyclo[2.2.2]oct-3-yl)[Z-3-(2-thienylthio)propenamide] and (R)-N-(1-Aza-bicyclo[2.2.2]oct-3-yl)[E-3-(2-thienylthio)propenamide]

Employing essentially the same procedure as that described in Example 1 above but substituting 3-(2-thienylthio)acrylic acid for the 3-(phenylthio)acrylic acid and purifying by chromatography on silica gel using ammoniated methanol/chloroform mixtures as the eluent resulted in formation of the title compounds; MS (ES+) 295. (MH+).

Example 20

(R)-N-(1-Aza-bicyclo[2.2.2]oct-3-yl)[Z-3-(2-benzoxazolylthio)propenamide] and (R)-N-(1-Aza-bicyclo[2.2.2]oct-3-yl)[E-3-(2-benzoxazolylthio)propenamide]

Employing essentially the same procedure as that described in Example 1 above but substituting 3-(2-benzoxazolylthio)acrylic acid for the 3-(phenylthio)acrylic acid and purifying by chromatography on silica gel using ammoniated methanol/chloroform mixtures as the eluent resulted in formation of the title compounds; MS (ES+) 330. (MH+).

Example 21

(R)-N-(1-Aza-bicyclo[2.2.2]oct-3-yl)[Z-3-(4-trifluoromethyl-2-pyrimidinylthio)propenamide]

Employing, essentially the same procedure as that described in Example 1 above but substituting 3-(4-trifluoromethyl-2-pyrimidinylthio)acrylic acid for the 3-(phenylthio)acrylic acid and purifying by chromatography on silica gel using ammoniated methanol/chloroform mixtures as the eluent resulted in formation of the title compound; MS (ES+) 359. (MH+).

Example 22

(R)-N-(1-Aza-bicyclo[2.2.2]oct-3-yl)[Z-3-(4-fluorophenylthio)propenamide] and (R)-N-(1-Aza-bicyclo[2.2.2]oct-3-yl)[E-3-(4-fluorophenylthio)propenamide]

Employing essentially the same procedure as that described in Example 1 above but substituting 3-(4-fluorophenylthio)acrylic acid for the 3-(phenylthio)acrylic acid and purifying by chromatography on silica gel using ammoniated methanol/chloroform mixtures as the eluent resulted in formation of the title compounds; MS (ES+) 307. (MH+).

Example 23

(R)-N-(1-Aza-bicyclo[2.2.2]oct-3-yl)[Z-3-(2-thiazolo[4,5-b]pyridylthio)propenamide] and (R)-N-(1-Aza-bicyclo[2.2.2]oct-3-yl)[E-3-(2-thiazolo[4,5-b]pyridylthio)propenamide]

Employing essentially the same procedure as that described in Example 1 above but substituting 3-(2-thiazolo[4,5-b]pyridylthio)acrylic acid for the 3-(phenylthio)acrylic acid and purifying by chromatography on silica gel using ammoniated methanol/chloroform mixtures as the eluent resulted in formation of the title compounds; MS (ES+) 347. (MH+).

Example 24

(R)-N-(1-Aza-bicyclo[2.2.2]oct-3-yl)[Z-3-(3-fluorophenylthio)propenamide] and (R)-N-(1-Aza-bicyclo[2.2.2]oct-3-yl)[E-3-(3-fluorophenylthio)propenamide]

Employing essentially the same procedure as that described in Example 1 above but substituting 3-(3-fluorophenylthio)acrylic acid for the 3-(phenylthio)acrylic acid and purifying by chromatography on silica gel using ammoniated methanol/chloroform mixtures as the eluent resulted in formation of the title compounds; MS (ES+) 307. (MH+).

What is claimed is:

1. A compound of formula I,

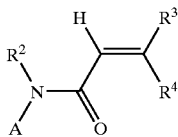

I wherein:

A represents:

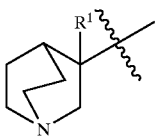

II

R represents hydrogen or methyl;
$R^1$ and $R^2$ are independently hydrogen, or $C_1$–$C_4$ alkyl;
$R^3$ and $R^4$ are independently hydrogen, $C_1$–$C_4$ alkyl or SAr, provided that at least one of $R^3$ and $R^4$ represents SAr;

Ar represents a 5- or 6-membered aromatic or heteroaromatic ring containing zero to three nitrogen atoms, zero or one oxygen atom, and zero or one sulfur atom or an 8-, 9- or 10-membered fused aromatic or heteroaromatic ring system containing zero to four nitrogen atoms, zero to one oxygen atom, and zero to one sulfur atom which may optionally be substituted with one or more substituents selected from: hydrogen, halogen, $C_1$–$C_4$ alkyl, $C_2$–$C_4$ alkenyl, $C_2$–$C_4$ alkynyl, aryl, heteroaryl, —$CO_2R^5$, —CN, —$NO_2$, —$NR^6R^7$, —$CF_3$, 13 $OR^8$;

$R^5$, $R^6$, $R^7$, and $R^8$ are independently hydrogen, $C_1$–$C_4$ alkyl, aryl, heteroaryl, —(O)$R^9$, —C(O)NHR$^{10}$, —C(O)R$^{11}$, —SO$_2$R$^{12}$; or, $R^6$ and $R^7$ may together be $(CH_2)_jQ(CH_2)_k$ where Q is O, S, NR$^{13}$ or a bond;

j is 2 to 7;

k is 0 to 2;

$R^9$, $R^{10}$, $R^{11}$, $R^{12}$, and $R^{13}$, are independently $C_1$–$C_4$ alkyl, aryl, or heteroaryl;

or an enantiomer thereof, or a pharmaceutically-acceptable salt thereof.

2. A compound according to claim 1, wherein $R^1$, $R^2$, and one of $R^3$ or $R^4$ are hydrogen.

3. A compound according to claim 1, wherein Ar is a 5- or 6-membered aromatic or heteroaromatic ring containing zero to three nitrogen atoms, zero or one oxygen atom, and zero or one sulfur atom, which may optionally be substituted with one or more substituents selected from: hydrogen, halogen, $C_1$–$C_4$ alkyl, $C_2$–$C_4$ alkenyl, $C_2$–$C_4$ alkynyl, —$CO_2R^5$, —CN, —$NO_2$, —$NR^6R^7$, —$CF_3$, —$OR^8$.

4. A compound according to claim 3, wherein Ar is an heteroaromatic ring.

5. A compound according to claim 3, wherein Ar is a 6-membered aromatic or heteroaromatic ring containing zero to two nitrogen atoms.

6. A compound according to claim 3, wherein said aromatic or heteroaromatic ring is selected from phenyl, 2-pyridyl, or 2-pyrimidinyl.

7. A compound according to claim 1, said compound being:

N-(1-Aza-bicyclo[2.2.2]oct-3-yl)[Z-3-(phenylthio)propenamide]hydrochloride;
N-(1-Aza-bicyclo[2.2.2]oct-3-yl)[Z-3-(4-methylphenylthio)propenamide];
N-(1-Aza-bicyclo[2.2.2]oct-3-yl)[E-3-(4-methylphenylthio)propenamide];
N-(1-Aza-bicyclo[2.2.2]oct-3-yl)[Z-3-(3-methylphenylthio)propenamide];
N-(1-Aza-bicyclo[2.2.2]oct-3-yl)[E-3-(3-methylphenylthio)propenamide];
N-(1-Aza-bicyclo[2.2.2]oct-3-yl)[Z-3-(2-methylphenylthio)propenamide];
N-(1-Aza-bicyclo[2.2.2]oct-3-yl)[E-3-(2-methylphenylthio)propenamide];
N-(1-Aza-bicyclo[2.2.2]oct-3-yl)[Z-3-(4-methoxyphenylthio)propenamide];
N-(1-Aza-bicyclo[2.2.2]oct-3-yl)[E-3-(4-methoxyphenylthio)propenamide];
N-(1-Aza-bicyclo[2.2.2]oct-3-yl)[Z-3-(3-methoxyphenylthio)propenamide];
N-(1-Aza-bicyclo[2.2.2]oct-3-yl)[E-3-(3-methoxyphenylthio)propenamide];
N-(1-Aza-bicyclo[2.2.2]oct-3-yl)[Z-3-(2-methoxyphenylthio)propenamide];

N-(1-Aza-bicyclo[2.2.2]oct-3-yl)[E-3-(2-methoxyphenylthio)propenamide];
N-(1-Aza-bicyclo[2.2.2]oct-3-yl)[Z-3-(2-pyridylthio)propenamide];
N-(1-Aza-bicyclo[2.2.2]oct-3-yl)[E-3-(2-pyridylthio)propenamide];
N-(1-Aza-bicyclo[2.2.2]oct-3-yl)[Z-3-(4-pyridylthio)propenamide];
N-(1-Aza-bicyclo[2.2.2]oct-3-yl)[E-3-(4-pyridylthio)propenamide];
N-(1-Aza-bicyclo[2.2.2]oct-3-yl)[Z-3-(2-pyrimidinylthio)propenamide];
N-(1-Aza-bicyclo[2.2.2]oct-3-yl)[E-3-(2-pyrimidinylthio)propenamide];
N-(1-Aza-bicyclo[2.2.2]oct-3-yl)[Z-3-(2-methyl-3-furanylthio)propenamide];
N-(1-Aza-bicyclo[2.2.2]oct-3-yl)[E-3-(2-methyl-3-furanylthio)propenamide];
N-(1-Aza-bicyclo[2.2.2]oct-3-yl)[E-3-(2-imidazolylthio)propenamide];
N-(1-Aza-bicyclo[2.2.2]oct-3-yl)[Z-3-(phenylthio)-3-(methyl)propenamide];
N-(1-Aza-bicyclo[2.2.2]oct-3-yl)[Z-3-(2-benzothiazolylthio)propenamide];
N-(1-Aza-bicyclo[2.2.2]oct-3-yl)[E-3-(2-benzothiazolylthio)propenamide];
N-(1-Aza-bicyclo[2.2.2]oct-3-yl)[Z-3-(1-methyl-2-imidazolylthio)propenamide];
N-(1-Aza-bicyclo[2.2.2]oct-3-yl)[E-3-(1-methyl-2-imidazolylthio)propenamide];
N-(1-Aza-bicyclo[2.2.2]oct-3-yl)[Z-3-(5-methyl-1,3,4-thiadiazol-2-ylthio)propenamide];
N-(1-Aza-bicyclo[2.2.2]oct-3-yl)[E-3-(5-methyl-1,3,4-thiadiazol-2-ylthio)propenamide];
N-(1-Aza-bicyclo[2.2.2]oct-3-yl)[Z-3-(4-chlorophenylthio)propenamide];
N-(1-Aza-bicyclo[2.2.2]oct-3-yl)[Z-3-(2-thiazolylthio)propenamide];
N-(1-Aza-bicyclo[2.2.2]oct-3-yl)[Z-3-(2-thienylthio)propenamide];
N-(1-Aza-bicyclo[2.2.2]oct-3-yl)[E-3-(2-thienylthio)propenamide];
N-(1-Aza-bicyclo[2.2.2]oct-3-yl)[Z-3-(2-benzoxazolylthio)propenamide];
N-(1-Aza-bicyclo[2.2.2]oct-3-yl)[E-3-(2-benzoxazolylthio)propenamide];
N-(1-Aza-bicyclo[2.2.2]oct-3-yl)[Z-3-(4-trifluoromethyl-2-pyrimidinylthio)propenamide];
N-(1-Aza-bicyclo[2.2.2]oct-3-yl)[Z-3-(4-fluorophenylthio)propenamide];
N-(1-Aza-bicyclo[2.2.2]oct-3-yl)[E-3-(4-fluorophenylthio)propenamide];
N-(1-Aza-bicyclo[2.2.2]oct-3-yl)[Z-3-(2-thiazolo[4,5-b]pyridylthio)propenamide];
(R)-N-(1-Aza-bicyclo[2.2.2]oct-3-yl)[E-3-(2-thiazolo[4,5-b]pyridylthio)propenamide];
N-(1-Aza-bicyclo[2.2.2]oct-3-yl)[Z-3-(3-fluorophenylthio)propenamide], or
N-(1-Aza-bicyclo[2.2.2]oct-3-yl)[E-3-(3-fluorophenylthio)propenamide], or an enantiomer thereof, or a pharmaceutically-acceptable salt thereof.

8. A compound according to claim 1, said compound being:

(R)-N-(1-Aza-bicyclo[2.2.2]oct-3-yl)[Z-3-(phenylthio)propenamide]hydrochloride;

(R)-N-(1-Aza-bicyclo[2.2.2]oct-3-yl)[Z-3-(4-methylphenylthio)propenamide];
(R)-N-(1-Aza-bicyclo[2.2.2]oct-3-yl)[E-3-(4-methylphenylthio)propenamide];
(R)-N-(1-Aza-bicyclo[2.2.2]oct-3-yl)[Z-3-(3-methylphenylthio)propenamide];
(R)-N-(1-Aza-bicyclo[2.2.2]oct-3-yl)[E-3-(3-methylphenylthio)propenamide];
(R)-N-(1-Aza-bicyclo[2.2.2]oct-3-yl)[Z-3-(2-methylphenylthio)propenamide];
(R)-N-(1-Aza-bicyclo[2.2.2]oct-3-yl)[E-3-(2-methylphenylthio)propenamide];
(R)-N-(1-Aza-bicyclo[2.2.2]oct-3-yl)[Z-3-(4-methoxyphenylthio)propenamide];
(R)-N-(1-Aza-bicyclo[2.2.2]oct-3-yl)[E-3-(4-methoxyphenylthio)propenamide];
(R)-N-(1-Aza-bicyclo[2.2.2]oct-3-yl)[Z-3-(3-methoxyphenylthio)propenamide];
(R)-N-(1-Aza-bicyclo[2.2.2]oct-3-yl)[E-3-(3-methoxyphenylthio)propenamide];
(R)-N-(1-Aza-bicyclo[2.2.2]oct-3-yl)[Z-3-(2-methoxyphenylthio)propenamide];
(R)-N-(1-Aza-bicyclo[2.2.2]oct-3-yl)[E-3-(2-methoxyphenylthio)propenamide];
(R)-N-(1-Aza-bicyclo[2.2.2]oct-3-yl)[Z-3-(2-pyridylthio)propenamide];
(R)-N-(1-Aza-bicyclo[2.2.2]oct-3-yl)[E-3-(2-pyridylthio)propenamide];
(R)-N-(1-Aza-bicyclo[2.2.2]oct-3-yl)[Z-3-(4-pyridylthio)propenamide];
(R)-N-(1-Aza-bicyclo[2.2.2]oct-3-yl)[E-3-(4-pyridylthio)propenamide];
(R)-N-(1-Aza-bicyclo[2.2.2]oct-3-yl)[Z-3-(2-pyrimidinylthio)propenamide];
(R)-N-(1-Aza-bicyclo[2.2.2]oct-3-yl)[E-3-(2-pyrimidinylthio)propenamide];
(R)-N-(1-Aza-bicyclo[2.2.2]oct-3-yl)[Z-3-(2-methyl-3-furanylthio)propenamide];
(R)-N-(1-Aza-bicyclo[2.2.2]oct-3-yl)[E-3-(2-methyl-3-furanylthio)propenamide];
(R)-N-(1-Aza-bicyclo[2.2.2]oct-3-yl)[E-3-(2-imidazolylthio)propenamide];
(R)-N-(1-Aza-bicyclo[2.2.2]oct-3-yl)[Z-3-(phenylthio)-3-(methyl)propenamide];
(R)-N-(1-Aza-bicyclo[2.2.2]oct-3-yl)[Z-3-(2-benzothiazolylthio)propenamide];
(R)-N-(1-Aza-bicyclo[2.2.2]oct-3-yl)[E-3-(2-benzothiazolylthio)propenamide];
(R)-N-(1-Aza-bicyclo[2.2.2]oct-3-yl)[Z-3-(1-methyl-2-imidazolylthio)propenamide];
(R)-N-(1-Aza-bicyclo[2.2.2]oct-3-yl)[E-3-(1-methyl-2-imidazolylthio)propenamide];
(R)-N-(1-Aza-bicyclo[2.2.2]oct-3-yl)[Z-3-(5-methyl-1,3,4-thiadiazol-2-ylthio)propenamide];
(R)-N-(1-Aza-bicyclo[2.2.2]oct-3-yl)[E-3-(5-methyl-1,3,4-thiadiazol-2-ylthio)propenamide];
(R)-N-(1-Aza-bicyclo[2.2.2]oct-3-yl)[Z-3-(4-chlorophenylthio)propenamide];
(R)-N-(1-Aza-bicyclo[2.2.2]oct-3-yl)[Z-3-(2-thiazolylthio)propenamide];
(R)-N-(1-Aza-bicyclo[2.2.2]oct-3-yl)[Z-3-(2-thienylthio)propenamide];
(R)-N-(1-Aza-bicyclo[2.2.2]oct-3-yl)[E-3-(2-thienylthio)propenamide];
(R)-N-(1-Aza-bicyclo[2.2.2]oct-3-yl)[Z-3-(2-benzoxazolylthio)propenamide];
(R)-N-(1-Aza-bicyclo[2.2.2]oct-3-yl)[E-3-(2-benzoxazolylthio)propenamide];

(R)-N-(1-Aza-bicyclo[2.2.2]oct-3-yl)[Z-3-(4-trifluoromethyl-2-pyrimidinylthio)propenamide];

(R)-N-(1-Aza-bicyclo[2.2.2]oct-3-yl)[Z-3-(4-fluorophenylthio)propenamide];

(R)-N-(1-Aza-bicyclo[2.2.2]oct-3-yl)[E-3-(4-fluorophenylthio)propenamide];

(R)-N-(1-Aza-bicyclo[2.2.2]oct-3-yl)[Z-3-(2-thiazolo[4,5-b]pyridylthio)propenamide];

(R)-N-(1-Aza-bicyclo[2.2.2]oct-3-yl)[E-3-(2-thiazolo[4,5-b]pyridylthio)propenamide];

(R)-N-(1-Aza-bicyclo[2.2.2]oct-3-yl)[Z-3-(3-fluorophenylthio)propenamide], or (R)-N-(1-Aza-bicyclo[2.2.2]oct-3-yl)[E-3-(3-fluorophenylthio)propenamide], or an enantiomer thereof, or a pharmaceutically-acceptable salt thereof.

9. A compound according to claim 1, said compound being:

(R)-N-(1-Aza-bicyclo[2.2.2]oct-3-yl)[Z-3-(2-pyridylthio)propenamide];

(R)-N-(1-Aza-bicyclo[2.2.2]oct-3-yl)[E-3-(2-pyridylthio)propenamide], or (R)-N-(1-Aza-bicyclo[2.2.2]oct-3-yl)[Z-3-(2-pyrimidinylthio)propenamide], or an enantiomer thereof, or a pharmaceutically-acceptable salt thereof.

10. A pharmaceutical composition comprising a compound according to claim 1, in admixture with a pharmaceutically-acceptable diluent or carrier.

11. A method of treatment of disorders in which activation of the α7 nicotinic receptor is beneficial which comprises administering a therapeutically effective amount of a compound according to claim 1 to a subject having anxiety, jetlag, nicotine addiction, pain, or ulcerative colitis.

12. A method for inducing the cessation of smoking which comprises administering a therapeutically effective amount of a compound according to claim 1 to a subject having nicotine addiction or addiction to smoking.

* * * * *